US00PP12017P2

(12) United States Plant Patent
VandenBerg

(10) Patent No.: US PP12,017 P2
(45) Date of Patent: Jul. 24, 2001

(54) CHRYSANTHEMUM PLANT NAMED 'CONTACT'

(75) Inventor: Cornelis P. VandenBerg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/383,526

(22) Filed: Aug. 26, 1999

(51) Int. Cl.[7] ..... A01H 5/00

(52) U.S. Cl. ..... Plt./289
(58) Field of Search ..... Plt./289

*Primary Examiner*—Howard J. Locker
(74) *Attorney, Agent, or Firm*—C. A. Whealy

(57) ABSTRACT

A distinct cultivar of Chrysanthemum plant named 'Contact', characterized by its large decorative quilled-type inflorescences that are about 8.1 cm in diameter; attractive upright bright yellow ray florets; numerous inflorescences per stem; early flowering, response time about 53 days; dark green foliage; strong stems; and excellent postproduction longevity with inflorescences maintaining good substance and color for about four weeks in an interior environment.

3 Drawing Sheets

BACKGROUND OF THE INVENTION

The present invention relates to a new and distinct cultivar of Chrysanthemum plant, botanically known as *Dendranthema grandiflora* and referred to by the cultivar name Contact.

The new Chrysanthemum is a product of a planned breeding program conducted by the Inventor in Salinas, Calif. The objective of the breeding program is to create new cut Chrysanthemum cultivars having inflorescences with desirable colors and good form and substance.

The new Chrysanthemum originated from a cross made by the Inventor in January, 1993, in Salinas, Calif., of a proprietary Chrysanthemum seedling selection identified as 1425, as the female, or seed, parent with a proprietary Chrysanthemum seedling selection identified as 3696, as the male, or pollen, parent.

The cultivar Contact was discovered and selected by the Inventor as a flowering plant within the progeny of the stated cross in a controlled environment in Alva, Fla., in March, 1994. The selection of this plant was based on its desirable inflorescence color and good form and substance.

Asexual reproduction of the new Chrysanthemum by terminal cuttings taken in a controlled environment in Alva, Fla., has shown that the unique features of this new Chrysanthemum are stable and reproduced true to type in successive generations.

SUMMARY OF THE INVENTION

The cultivar Contact has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Contact'. These characteristics in combination distinguish 'Contact' as a new and distinct cultivar:

1. Large decorative quilled-type inflorescences that are about 8.1 cm in diameter.
2. Attractive upright bright yellow ray florets.

3. Numerous inflorescences per stem.
4. Early flowering.
5. Dark green foliage.
6. Strong stems.
7. Excellent postproduction longevity with inflorescences maintaining good substance and color for about four weeks in an interior environment.

BRIEF DESCRIPTION OF THE PHOTOGRAPHS

The accompanying colored photographs illustrate the overall appearance of the new Chrysanthemum, showing the colors as true as it is reasonably possible to obtain in colored reproductions of this type.

The photograph on the first sheet comprises a side perspective view of a typical flowering stem of 'Contact' grown as a spray-type cut Chrysanthemum.

The photograph on the second sheet comprises a top perspective view of typical inflorescences of the cultivar Contact.

The photograph at the top of the third sheet comprises a close-up view of upper and lower surfaces of typical inflorescences of the cultivar Contact.

The photograph at the bottom of the third sheet comprises a close-up view of typical young and mature leaves of the cultivar Contact. Floret and foliage colors in the photographs may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., under conditions which approximate commercial practice in a double-layer polyethylene-covered greenhouse. Two-week old rooted cuttings were planted on Feb. 11, 1999 and received 21 long day/short nights followed by short day/long nights until flowering. Plants were grown as single-stem cut chrysanthemums. During the production time, the following environmental conditions were measured: day temperatures ranging from 18 to 27° C.; night temperatures ranging from 16 to 18° C.; and light level of about 2,000 to 4,000 foot candles. Measurements and numerical values represent averages for six to ten typical flowering stems.

Botanical classification: *Dendranthema grandiflora* cultivar Contact.

Commercial classification: Decorative quilled spray-type cut Chrysanthemum with tubular ray florets.

Parentage:

*Female or seed parent.*—Proprietary *Dendranthema grandiflora* seedling selection, code number 1425.

*Male or pollen parent.*—Proprietary *Dendranthema grandiflora* seedling selection, code number 3696.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous decorative quilled spray-type cut flower. Stems upright, uniform habit and freely branching.

*Flowering stem length.*—About 89 cm.

*Stem color.*—144A.

*Foliage description.*—Arrangement: Alternate. Length: About 12.2 cm. Width: About 8.5 cm. Apex: Mucronate. Base: Truncate. Margin: Palmately lobed. Texture: Upper and lower surfaces slightly pubescent. Veins prominent on lower surface. Color: Young foliage upper surface: 147A. Young foliage lower surface: Darker than 147B. Mature foliage upper surface: 147A. Mature foliage lower surface: 147B. Venation upper surface: 147B. Venation lower surface: 147B. Petiole: Length: About 3.5 cm. Diameter: About 3 mm. Color: Upper, 147B–147C; lower, 147B; margins, 147A.

Flowering description:

*Appearance.*—Decorative quilled spray-type inflorescence form with tubular ray florets. Inflorescences borne on terminals, arising from leaf axils. Disc and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about 53 days later.

*Postproduction longevity.*—In an interior environment, flowering stems will maintain good color and substance for about four weeks in an interior environment after one week of cool storage.

*Quantity of inflorescences.*—Numerous, about 12 inflorescences per flowering stem.

*Inflorescence size.*—Diameter: About 8.1 cm. Depth (height): About 2.3 cm. Diameter of disc: No disc florets observed. Diameter of receptacle: About 8 mm.

*Ray florets.*—Shape: Tubular, quilled. Length: About 4.8 cm. Width: About 4 mm. Apex: Pointed, acute or dentate. Base: Fused. Margin: Tubular. Texture: Smooth, glabrous; durable. Aspect: Upright, about 30° to peduncle. Number of ray florets per inflorescence: Numerous, very full inflorescences, typically about 210. Color: When opening, tube: 5A. When opening, throat: 5A. Mature, tube: 5A to 5C. Mature, throat: 5A.

*Peduncle.*—Aspect: Strong and angled about 35 to 40° to the stem. Length: First peduncle: About 9.75 cm. Fourth peduncle: About 14.8 cm. Seventh peduncle: About 20.2 cm. Texture: Very fine pubescence. Color: 144A.

*Reproductive organs.*—Androecium: None, no disc florets observed. Gynoecium: Present on both ray and disc florets.

Disease resistance: Resistance to diseases common to Chrysanthemums has not been observed on plants grown under commercial conditions.

Temperature tolerance: Plants of the new Chrysanthemum have demonstrated good tolerance to temperatures as low as 5° C.

Seed production: Seed production has not been observed.

It is claimed:

1. A new and distinct cultivar of Chrysanthemum plant named 'Contact', as illustrated and described.

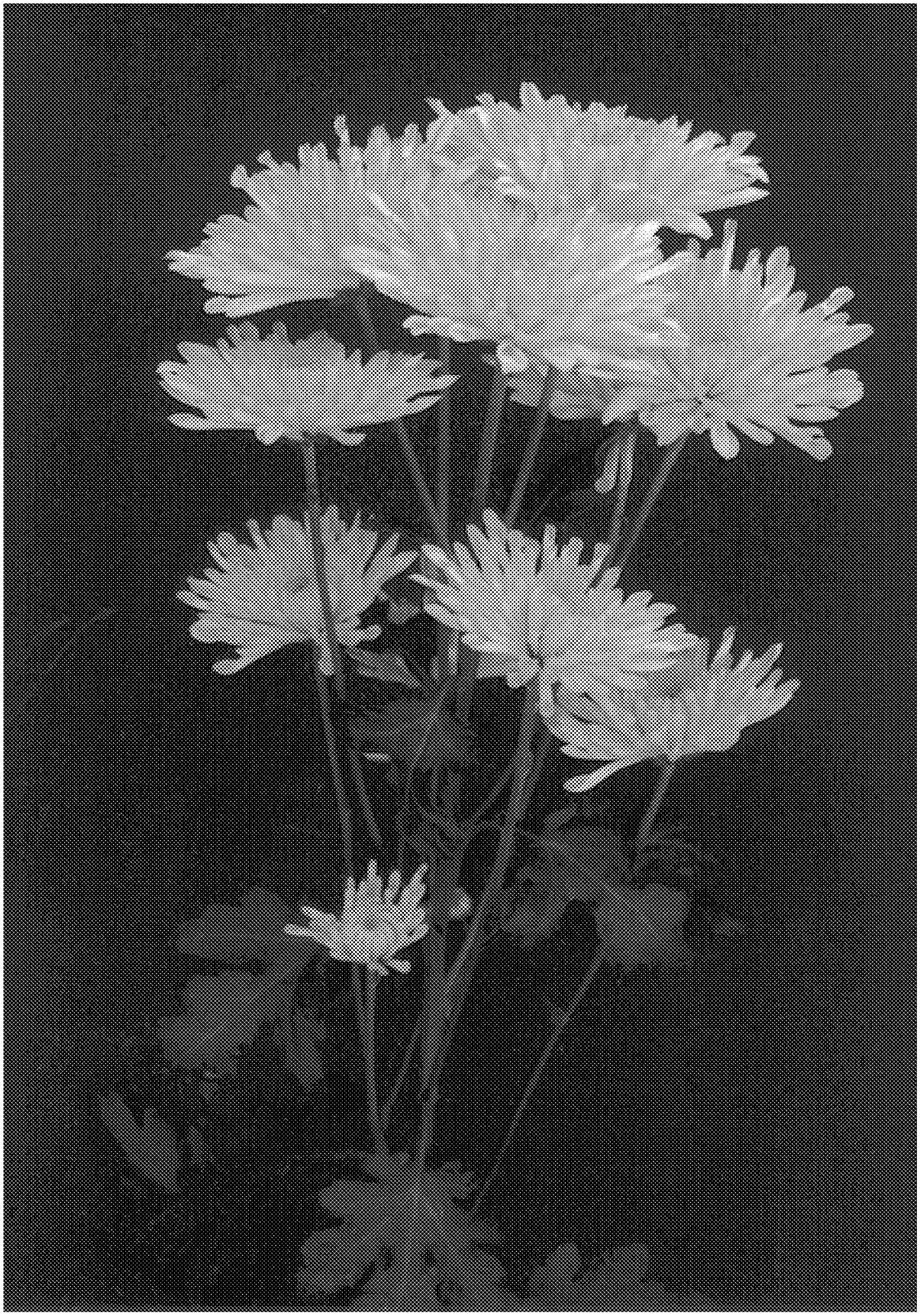

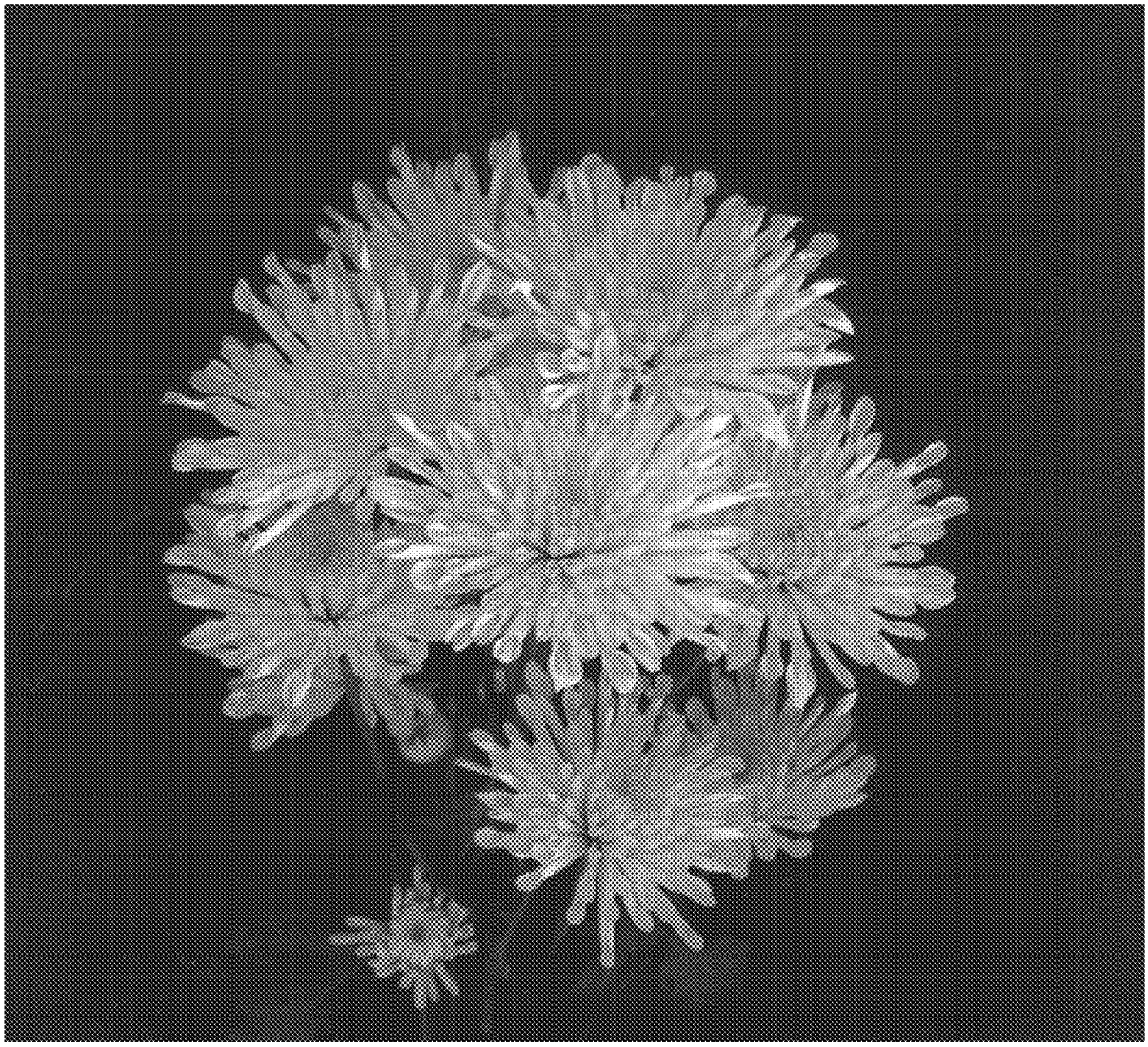

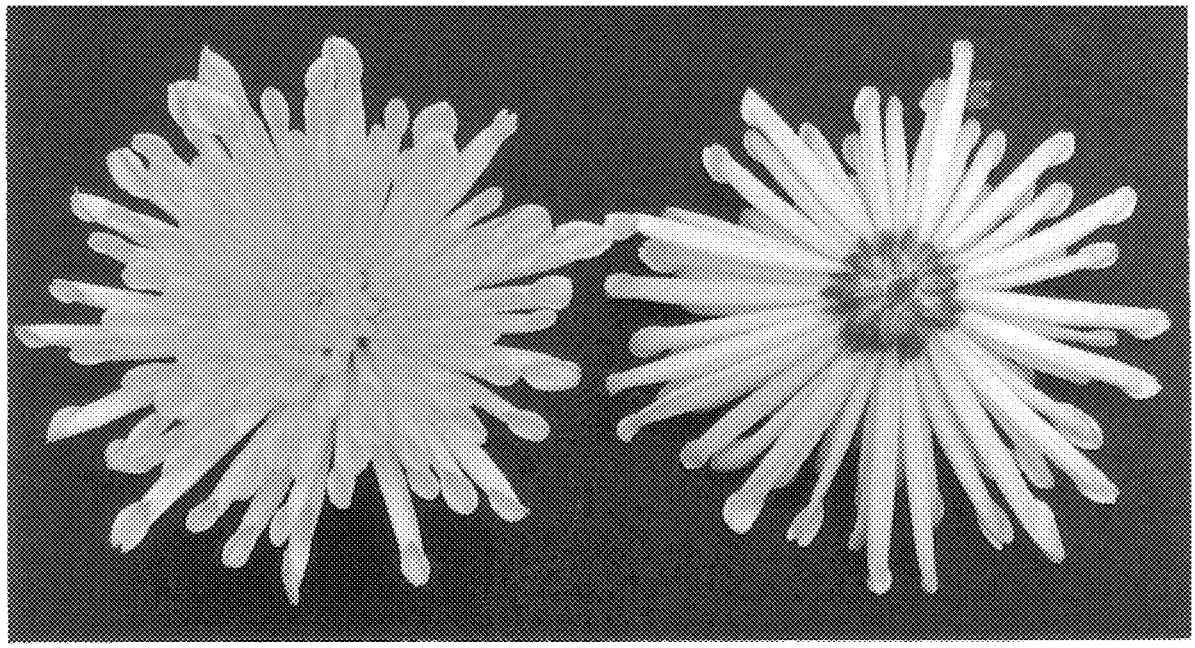
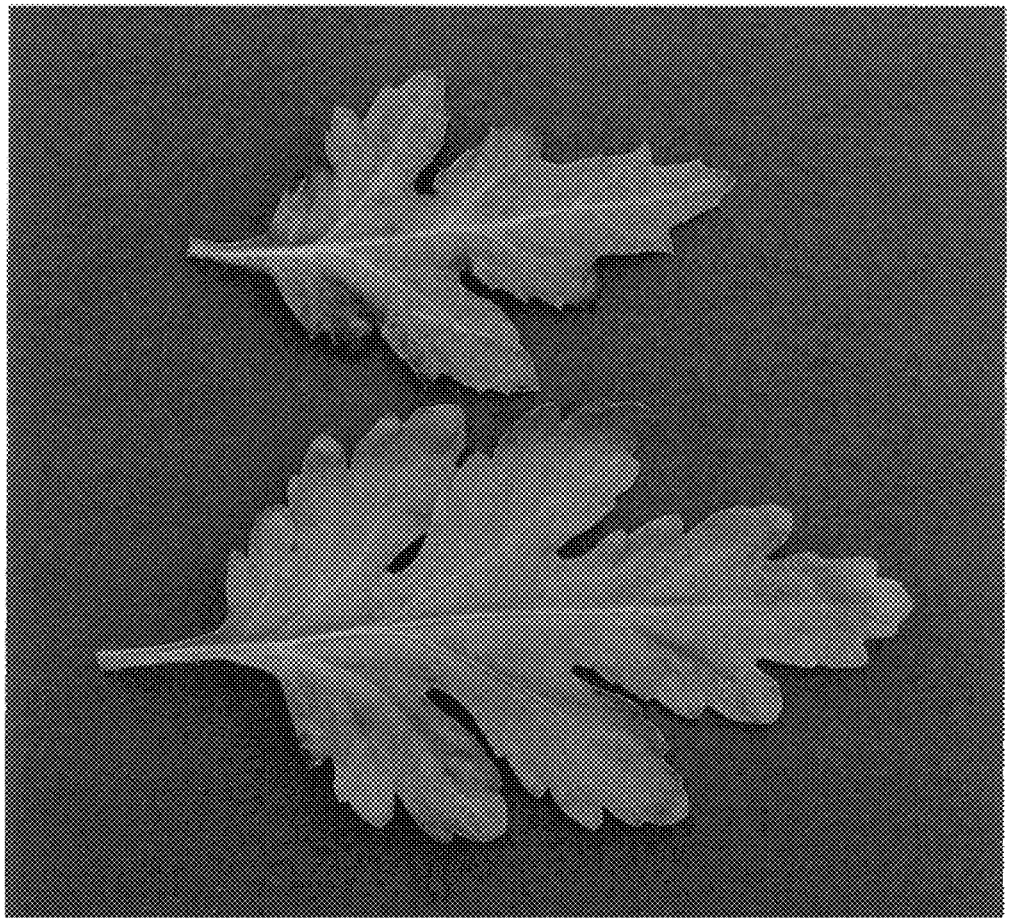

* * * * *